(12) United States Patent
Van Der Krieken et al.

(10) Patent No.: US 10,342,235 B2
(45) Date of Patent: Jul. 9, 2019

(54) FORMULATIONS COMPRISING PHOSPHITE

(71) Applicant: Ceradis B.V., Wageningen (NL)

(72) Inventors: Wilhelmus Maria Van Der Krieken, Wageningen (NL); Christiaan Gerardus Johannes Maria Jans, Wageningen (NL); Wilhelmus Bernardus Albertus Hendrikus Rutten, Wageningen (NL)

(73) Assignee: Ceradis B.V., Wageningen (NL)

( * ) Notice: Subject to any disclaimer, the term of this patent is extended or adjusted under 35 U.S.C. 154(b) by 0 days.

(21) Appl. No.: 15/746,285

(22) PCT Filed: Jul. 21, 2016

(86) PCT No.: PCT/NL2016/050543
§ 371 (c)(1),
(2) Date: Jan. 19, 2018

(87) PCT Pub. No.: WO2017/014633
PCT Pub. Date: Jan. 26, 2017

(65) Prior Publication Data
US 2018/0228161 A1    Aug. 16, 2018

(30) Foreign Application Priority Data
Jul. 21, 2015 (NL) ..................................... 2015200

(51) Int. Cl.
| | |
|---|---|
| *A01N 59/26* | (2006.01) |
| *A01N 25/04* | (2006.01) |
| *A01N 25/30* | (2006.01) |
| *A01N 57/12* | (2006.01) |
| *C05G 3/06* | (2006.01) |
| *C05B 17/00* | (2006.01) |
| *C05G 3/00* | (2006.01) |
| *C07F 9/38* | (2006.01) |

(52) U.S. Cl.
CPC .............. *A01N 59/26* (2013.01); *A01N 25/04* (2013.01); *A01N 25/30* (2013.01); *A01N 57/12* (2013.01); *C05B 17/00* (2013.01); *C05G 3/007* (2013.01); *C05G 3/06* (2013.01); *C07F 9/38* (2013.01)

(58) Field of Classification Search
None
See application file for complete search history.

(56) References Cited

U.S. PATENT DOCUMENTS 4,075,324 A    2/1978    Thizy et al.

FOREIGN PATENT DOCUMENTS

| EP | 1655275 A2 | 10/2006 |
| WO | 2008069826 A1 | 6/2008 |
| WO | 2011065832 A2 | 6/2011 |

*Primary Examiner* — Alton N Pryor
(74) *Attorney, Agent, or Firm* — Arent Fox LLP

(57) ABSTRACT

The invention relates to an aqueous suspension comprising a solubilized salt and insolubilized ingredients such as lignosulfonate and a dodecyl sulfate salt. The invention further relates to methods of producing said aqueous suspension, and to methods to employ said suspension for fertilizing agricultural plants and for protecting a plant or plant part against a pathogen. The invention additionally relates to methods of preventing, reducing and/or eliminating the presence of a pathogen on a plant or plant part, and to methods for treatment of a soil, comprising providing a suspension according to the invention.

21 Claims, No Drawings

FORMULATIONS COMPRISING PHOSPHITE

FIELD

The invention relates to novel aqueous suspensions for use in agriculture. Said novel suspension comprises a solubilized phosphite salt and insolubilized components. Said suspensions can be used as fertilizers and/or as fungicides.

INTRODUCTION

Phosphites, or phosphonates, are compounds derived of phosphorous acid, H3PO3. In agriculture, phosphites are marketed as fertilizers and as fungicides. Phosphites are known as environmental benign fungicides with a low toxicity towards users and consumers.

The activity of phosphites as anti-fungal agent depends on a direct toxicity towards oomycetes like Phytophthora and Pythium and a stimulation of plant defense (Smillie, R., Grant, B. R., Guest, D. (1989). Phytopathology 79: 921-926; Daniel, R., Guest, D. (2006). Physiol. Mol. Plant. Pathol. 67: 194-201). To achieve an adequate control of plant diseases by phosphites, a sufficiently high concentration of phosphite in the plant tissue needs to be reached, which can only be attained by applying a high dose of phosphite (Pilbeam, R. A., Colquhoun, I. J., Shearer, B., Hardy, G. E. StJ. (2000). Australasian Plant Pathology 29: 86-95; Pajor, E., Le Corre, D., and Silué, D. (2001). European Journal of Plant Pathology 107: 861-869).

Phosphite was found to be toxic to plants when applied at high concentrations. This toxicity is enhanced if adjuvants such as spreaders, wetting agents and penetrant are combined with phosphite. These adjuvants normally help to optimize the behavior of a pesticide control agent and help the control agent to penetrate the leaf. The fact that phosphites cannot readily be used in combination with adjuvants, especially spreaders, wetting agents and penetrant compounds, reduces the potential efficacy of phosphite products.

The limitation of the use of adjuvants in combination with phosphites also limits the possibilities of combining phosphite products in tank mixes with other pesticides that may contain phytotoxicity-enhancing adjuvants. In addition, it is generally known that phosphite products are not compatible with alkaline materials such as lime, sulfur or dormant spray oils, and that spraying concurrently with zinc, copper or other metals should be avoided, as is indicated on the product labels of commercially available phosphite products.

From this it is clear that there is a demand for a new formulation for phosphite products, allowing the use of phosphites in combination with other fertilizers and/or pesticides.

There thus is a need in the art for stable, concentrated fertilizer and fungicide compositions that are compatible with other agricultural products. Such compositions should also be easy to pour from a container. The present invention fulfills these needs, as well as others.

The invention therefore provides an aqueous suspension comprising a solubilized phosphite salt as fertilizer and/or fungicide at 20-70% (w/w), insolubilized lignosulfonate at 2-20% (w/w), a dodecyl sulfate salt as an insolubilized anionic surfactant at 0.5-10% (w/w), and an ethylene oxide/propylene oxide block copolymer at 0.2-5% (w/w).

It was found by the present inventors that a dodecyl sulfate salt as an insolubilized anionic surfactant and lignosulfonate remain stable in the suspension, when present with an solubilized phosphite salt and an ethylene oxide/propylene oxide block copolymer. The presence of anionic surfactant and lignosulfonate was found to reduce crystallization of the solubilized salt during the production of the aqueous suspension.

A person skilled in the art will understand that other anionic surfactants such as, for example, ammonium lauryl sulfate, dioctyl sodium sulfosuccinate, perfluorobutanesulfonic acid, perfluorononanoic acid, perfluorooctanesulfonic acid, perfluorooctanoic acid, potassium lauryl sulfate, sodium dodecyl sulfate, sodium dodecylbenzenesulfonate, sodium laureth sulfate, sodium lauroyl sarcosinate, sodium myreth sulfate, sodium octyl sulfate, sodium tetradecyl sulfate, sodium pareth sulfate and sodium stearate, might also be suited as an insolubilized anionic surfactant in a suspension according to the invention.

The high fertilizer and/or fungicide solubilized phosphite salt concentration enables the efficient packaging of the aqueous suspension at a minimal volume, thereby reducing packaging and transporting costs. However, the high fertilizer and/or fungicide phosphite salt concentration prevents the solubilization of the lignosulfonate and the anionic surfactant which, by themselves, have a good solubility in an aqueous suspension. Surprisingly, the suspension comprising a solubilized phosphite salt and ethylene oxide/propylene oxide block copolymer, in the presence of a dodecyl sulfate salt as an insolubilized anionic surfactant and insolubilized lignosulfonate, was found to remain stable in standard storage tests. To date, there are no liquid crop protection products containing undissolved lignosulfonate, because lignosulfonate dissolves very well in an aqueous solution up to 500 gram/liter.

In addition, a diluted suspension was found to be compatible with other products, including metal-containing products, presumably because substances that may react or interfere with the phosphite salt are captured by the combination of anionic surfactant and lignosulfonate, thereby preventing flocculation and/or sedimentation.

Furthermore, other substances that may be introduced in the suspension, for example by dilution of the suspension in a tank mix with ditchwater, are captured by the anionic surfactant and lignosulfonate.

Methods for determining the stability of a composition are known in the art and include accelerated storage tests by heating, according to CIPAC MT 46.1, MT 46.2, and MT 46.3.

The term "aqueous suspension", as is used herein, refers to a suspension of insoluble particles in a liquid that substantially comprises water. Said suspension preferably is a water slurriable powder (WS), or, more preferred, a suspension concentrate (SC). The term "substantially" indicates that the main constituent of the liquid is water, but the liquid may contain, for example, an oily substance up to a maximum of about 2% (v/v).

Said suspension preferably is a fertilizer.

The term phosphite, as is used herein, refers to a compound that comprises a phosphite group, or a compound which allows the release of a phosphite ion such as the commercial ethyl hydrogen phosphonate product called Aliette® (Bayer, Germany). The term phosphite includes compounds such as phosphorous acid and phosphonic acid as well as derivatives thereof such as esters and/or alkali metal or alkaline earth metal salts thereof.

Phosphite has been known for its fertilizer properties since at least the 1990s, as is described in U.S. Pat. No. 5,514,200. Prior to this discovery, phosphite was allowed only for use as a fungicide (U.S. Pat. No. 4,075,324) and as a food preservative in the USA. Unlike sulfate and phosphate, phosphite is readily absorbed by the leaves. Because of this, phosphite can be an excellent fertilizer material for use in foliar applications. In addition, phosphite is mobile in the soil and readily moves to the roots to become absorbed by the plant. Because of this, phosphite is an excellent stable, slow release, fertilizer material for use in soil and plant applications.

Phosphites, such as potassium phosphite, have shown low toxicity in rodents after oral administration as well as after dermal administration and inhalatory exposure. No safety concerns are known for operators and bystanders, nor for consumers. Phosphonates are neither skin sensitizers nor skin or eye irritants (EFSA J, 2012. 10(12): 2963).

Suitable examples of phosphite containing compounds are phosphorous acid and its (alkali metal or alkaline earth metal) salts such as potassium phosphites e.g. KH2P03 and K2HP03, sodium phosphites and ammonium phosphites, and (C-C4) alkyl esters of phosphorous acid and their salts such as aluminum ethyl phosphite (fosetyl-AI), calcium ethyl phosphite, magnesium isopropyl phosphite, magnesium isobutyl phosphite, magnesium sec-butyl phosphite and aluminum N-butyl phosphite.

A preferred phosphite is a phosphite salt such as KH2PO3, K2HPO3, NaH2PO3, Na2HPO3, (NH4)2HPO3, (NH4)H2PO3, and mixtures of these compounds. A mixture of KH2PO3 and K2HPO3 is suitably obtained by adding KOH or K2CO3 to a KH2PO3 composition at a final pH of 4-9.

Said phosphite, preferably bisodium hydrogen phosphite, is preferably present in a suspension according to the invention as a solubilized salt at 10-70% (w/w), preferably 20-50% (w/w), more preferred at about 40% (w/w).

A suspension according to the invention further comprises insolubilized lignosulfonate. Said lignosulfonate is preferably present as a lignosulfonate salt such as, for example, calcium lignosulfonate, sodium lignosulfonate, potassium lignosulfonate, ammonium lignosulfonate, magnesium lignosulfonate and mixtures thereof.

Said lignosulfonate, preferably calcium lignosulfonate, is present in a relative amount of between 2-30% (w/w), preferably between 5-20% (w/w), preferably about 10% (w/w), such as 9% (w/w), 10% (w/w) and 11% (w/w).

The insolubilized dodecyl sulfate salt as an anionic surfactant is preferably selected from the group consisting of ammonium dodecyl sulfate, sodium dodecyl sulfate, and potassium dodecyl sulfate. The latter is less preferred due to its low solubility. A preferred salt of dodecyl sulfate is sodium dodecyl sulfate such as, for example, HELIWET NLS 90 (Mosselman s.a., B-7011 Ghlin, Belgium). Said insolubilized dodecyl sulfate salt, preferably sodium dodecyl sulfate, is present at 0.5-10% (w/w), preferably at 1-5% (w/w), more preferred at about 1.5% (w/w).

The ethylene oxide/propylene oxide block copolymer in a suspension according to the invention preferably is polyoxypropylene that is flanked by two chains of polyoxyethylene. Because the lengths of the polymer blocks can be customized, many different ethylene oxide/propylene oxide block copolymers exist that have slightly different properties. These copolymers are commonly named with the letter "P" (for poloxamer) followed by three digits: the first two digits×100 give the approximate molecular mass of the polyoxypropylene core, and the last digit×10 gives the percentage polyoxyethylene content (e.g., P407 refers to a poloxamer with a polyoxypropylene molecular mass of 4,000 g/mol and a 70% polyoxyethylene content). For commercially available ethylene oxide/propylene oxide block copolymers, such as Pluronic® and Synperonic®, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content. Fore example, L61 indicates a polyoxypropylene molecular mass of 1,800 g/mol and a 10% polyoxyethylene content.

A preferred ethylene oxide/propylene oxide block copolymer has a molecular mass of about 2000 g/mol, having about 10% polyoxyethylene by weight, such as Synperonic PE/L61.

Said ethylene oxide/propylene oxide block copolymer, preferably sodium dodecyl sulfate, is present at 0.2-3% (w/w), preferably at 0.5-1.5% (w/w), more preferred at about 0.9% (w/w).

A most preferred aqueous suspension comprises a solubilized phosphite salt at 20-50% (w/w), insolubilized lignosulfonate at 2-30% (w/w), an insolubilized anionic surfactant at 0.5-10% (w/w), and an ethylene oxide/propylene oxide block copolymer at 0.2-3% (w/w).

A suspension according to the invention preferably comprises an anti-foaming agent. If present, said anti-foaming agent is preferably a polysilicic acid, meta-silicic acid, ortho-silicic acid, silica gel, silicic acid gels, kieselguhr, and/or, preferably, a linear polydimethylsiloxane, which has a compound of the formula HO—[Si(CH3)2—O—]n—H as its chemical backbone. A preferred polydimethylsiloxane has an average dynamic viscosity, measured at 25° C., in the range from 1000 to 8000 mPas (mPas=millipascal-second), preferably 1200 to 6000 mPas, more preferably about 1500 mPas. Examples of defoamers of this kind are Rhodorsil® Antifoam 416 and Rhodorsil® Antifoam 481, both obtainable from Rhodia. Said anti-foaming agent is preferably present at 0-1% (w/w), preferably at about 0.2% (w/w).

It is further preferred that a suspension according to the invention has an average particle size between 0.2 and 10 micrometer, preferably between 0.5 and 5 micrometer. Methods for determining the average particle size in a suspension are known to the skilled person. For example, Hukkanen and Braatz, 2003. Sensors and Actuators B 96: 451-459, discuss varies methods that can be used for determining the average particle size in a suspension, including forward light scattering and ultrasonic extinction. A preferred method is sieve analysis or gradation test, which is commonly used to assess the particle size distribution of a granular material.

In case the average particle size of a suspension is above 5 micrometer, the suspension is crushed, preferably by milling, to generate a suspension having an average particle size between 0.2 and 5 micrometer.

The pH of a suspension according to the invention preferably is between pH=6 and pH=10, more preferably between pH=7 and pH=9, more preferably about pH=8.5. If required, the pH can be adapted using, for example, HCl or NaOH, as is known to a person skilled in the art.

The invention further provides a method of producing an aqueous suspension, said method comprising providing a 10-50% (w/w) aqueous solution of a solubilized salt, adding 2-20% (w/w) of powderous lignosulfonate to said solution, adding 0.5-10% (w/w) of powderous dodecyl sulfate salt, and adding 0.2-2% (w/w) of an ethylene oxide/propylene oxide block copolymer.

The solubilized salt, lignosulfonate, dodecyl sulfate salt, and ethylene oxide/propylene oxide block copolymer are as defined herein above.

Said method further comprises crushing the resulting suspension to an average particle size of between 0.2 and 10 micrometer, preferably between 0.5 and 5 micrometer, preferably by milling, for example by using a bead mill apparatus such as Dyno-mill® (Glen Mills Inc. Clifton, N.J.).

The invention further provides a method of fertilizing an agricultural plant, comprising applying to said agricultural plant the suspension according to the invention.

Prior to use, a suspension according to the invention is preferably dissolved or dispersed in water or diluted with water to contain between 0.001 and 10 w/v % of phosphite. Upon dilution, the insolubilized dodecyl sulfate salt and lignosulfonate will dissolve to yield a diluted aqueous composition that is substantially a solution.

A fertilizer comprising a suspension according to the invention, or a dilution thereof, may be applied to an agricultural plant by foliar application but can also be applied by other methods such as irrigation and application to the soil in which the agricultural plant will be growing. The fertilizer is applied according to agricultural plant-specific recommendations which will depend upon the application method, time of application, rate of application, and product formulation. Agricultural plants that will benefit from the fertilizer include, but are not limited to, fruit crops, including citrus fruits such as orange, mandarin and lime, pome fruits such as apple and pear, stone fruits such as almond, apricot, cherry, damson, nectarine, tomato and watermelon, and tropical fruits such as banana, mango, lychee and tangerine; nuts, vegetables such as watermelon, tomatoes, peppers, and cucumbers; row crops such as cotton, corn and wheat, as well as other edible, commercial and ornamental plants.

A fertilizer comprising a suspension according to the invention, or a dilution thereof, is preferably applied through the use of a multiplicity spray tank. However, other methods for delivery of the fertilizer will be readily apparent to those of skill in the art.

A fertilizer comprising a suspension according to the invention, or a dilution thereof, may be mixed with other fertilizing and/or plant protection agents prior to applying the fertilizer to an agricultural plant, including nitrogen-based fertilizers such as ammonia and ammonium nitrate, and/or multi-nutrient fertilizers providing nitrogen, phosphorus, potassium and/or sulfur.

The invention further provides a method of protecting an agricultural plant or plant part against a pathogen, comprising applying to said agricultural plant or to said plant part a suspension according to the invention, or, preferably, a diluted aqueous composition thereof.

If required, a sticking agent is added to the diluted aqueous composition. Said diluted composition may be used, for example, to control powdery mildew and downy mildew infections of apples, gooseberries, hops, ornamentals, grapes, peaches, strawberries, soy bean, and sugar beets, scab, including common scab, apple scab, black scab on potatoes, pear scab, and powdery scab, brown rot of peaches, powdery mildew of apples, gooseberries, hops, ornamentals, grapes, peaches, strawberries, and sugar beets, apple scab, gall mite on blackcurrant, peanut leafspot, mildew on roses, and mites on beans, carrots, lucerne, melons, and tomatoes. For this, the aqueous composition is preferably sprayed over a plant, or part thereof.

Alternatively, a plant or part thereof is coated with a diluted composition comprising by submerging the plant or part thereof in the diluted composition to protect the plant of part thereof against a pathogen. A preferred part of a plant that is coated with a diluted composition according to the invention is seed, leaf or fruit.

Said fruit preferably is a citrus fruit such as orange, mandarin and lime, a pome fruit such as apple and pear, a stone fruit such as almond, apricot, cherry, damson, nectarine, tomato and watermelon; a tropical fruit such as banana, mango, lychee and tangerine. A preferred fruit is a citrus fruit, such as orange, or a tropical fruit such as banana.

A further preferred part that is coated with a diluted composition according to the invention is a post-harvest fruit, such as a citrus fruit such as orange, mandarin and lime, a pome fruit such as apple and pear, a stone fruit such as almond, apricot, cherry, damson, nectarine, tomato and watermelon; a tropical fruits such as banana, mango, lychee and tangerine. A preferred post-harvest fruit is a citrus fruit, such as orange, and a tropical fruit such as banana.

The invention further provides a method of preventing, reducing and/or eliminating the presence of a pathogen on a plant or on one or more plant parts, comprising applying to said plant or plant part the suspension according to the invention or a diluted aqueous composition thereof. A preferred plant part comprises seed, leaf or fruit, preferably a post-harvest fruit.

Said suspension, or diluted composition derived therefrom, is preferably mixed with a fungicide, preferably a metal-containing fungicide such as a copper-containing fungicide, a manganese-containing fungicide and/or a zinc-containing fungicide.

Said copper-containing fungicide preferably is a copper salt and/or a copper complex with organic molecules. Copper is most commonly used in fungicides in the form of copper hydroxide (Cu(OH)2), copper oxychloride (CuCl2.3Cu(OH)2) and Bordeaux mixture (CuSO4.3Cu (OH)2.3CaSO4), although a number of other salts and copper complexes of organic compounds are on the market or have been sold in the past.

Said manganese-containing fungicide preferably is selected from maneb (manganese ethylene bis dithiocarbamate), mancozeb (manganese-zinc ethylene bis(dithiocarbamate)), and zineb (zinc ethylene bis dithiocarbamate).

It was surprisingly found that a mixture of a suspension according to the invention, or a dilution thereof, with a metal-containing fungicide, remained stable and did not yield a precipitate. Said metal-containing fungicide is preferably mixed with a dilution of a suspension according to the invention, preferably in a tankmix prior to applying the mixture to a soil, plant or plant part.

The invention therefore provides a method according to the invention, wherein the suspension is diluted with an aqueous liquid, mixed with a metal-containing fungicide, prior to application to a soil, plant of plant part.

The invention further provides a method for treatment of a soil comprising providing the suspension according to the invention, or a diluted composition derived therefrom, and adding the suspension or diluted composition to the soil.

The diluted composition can be added directly to the soil according to any method known in the art e.g. by spraying it on the soil, mixing it through the soil, or by dipping the soil, or compounds which will be added to the soil, in the aqueous composition. In addition, the aqueous composition may also be added to an ingredient or to any composition applied to the soil, such as fertilizers, nutrient compositions and agents against other unwanted organisms such as insects, nematodes and/or mites.

A suspension according to the invention, or a diluted composition derived therefrom, may be applied at any suitable moment which of course will differ per crop and growth conditions such as the climate. It can e.g. be added to the soil before seeding or planting; before, during and/or after growth of the crop; and at different seasons such as before during and after the spring, summer, autumn and/or winter.

The suspension according to the invention, or a diluted composition derived therefrom, can be applied to an agricultural product such as a plant by spraying. Other methods suitable for applying the aqueous composition in liquid form to the products are also a part of the present invention. These include, but are not limited to, dipping, watering, drenching, introduction into a dump tank, vaporizing, atomizing, fogging, fumigating, painting, brushing, misting, dusting, foaming, spreading-on, packaging and coating {e.g. by means of wax or electrostatically). In addition, the suspension, or diluted composition derived therefrom, may also be injected into the soil. Spraying applications using automatic systems are known to reduce the labor costs and are cost-effective. Methods and equipment well-known to a person skilled in the art can be used for that purpose. The suspension, or diluted composition derived therefrom, can be regularly sprayed, when the risk of infection is high. When the risk of infection is lower spray intervals may be longer.

A suspension according to the invention, or a diluted composition derived therefrom, can also be used for treatment of soil. The suspension can be applied in/on any soil applied outside or inside such as in greenhouses. Said soil can be used for the production of any agricultural or horticultural product herein to be understood in a very broad sense and includes, but is not limited to edible crops such as cereals, vegetables, fruit, nuts/beans/seeds, herbs/spices and mushrooms; industrial crops; crops grown for feed; ornamental crops such as plants, flowers, bushes and trees.

Preferred examples of cereals are wheat, rice, oats, barley and maize. Preferred examples of vegetables are lettuce, beans, peas, cabbage, carrots, onions, potatoes, seed-potatoes, tomatoes, peppers, cucumbers, asparagus, paprika, aubergine and pumpkins. Preferred examples of fruit are apples, pears, cherries, peaches, apricots, plums, bananas, grapes, pineapples, papayas, mangos, kiwis, melons, oranges, grapefruits, lemons, mandarins, limes, strawberries, blackberries, currants, lychees, olives and avocados. Preferred examples of nuts, beans and seeds are peanuts, ground-nuts, almonds, cashew nuts, pistachio nuts, coconuts, coffee, cocoa, sunflowers and rapeseed. Preferred examples of industrial crops are sorghum, soya, palm oil, sugar beets, sugarcane, cotton, jute, tobacco, hops, rubber plants and tea.

A preferred soil is a growth substrate for mushrooms. In case of mushroom cultivation, a suspension according to the invention, or a diluted composition derived therefrom, can be mixed through the soil (e.g. compost) or sprayed on the soil and/or top-layer (e.g. the casing) at any stage of the production process of the soil and/or at any stage of the mushroom growth cycle such as: before during or after fermentation of the compost; after spawing; after casing; together with one or more of the watering steps; before, during and after pinning; after harvesting the first and/or second harvest; or any combination of the above mentioned stages. Said suspension, or dilution therefrom, can also be added to the spawn, the gypsum, the nutrient supplements and other additives usually applied in mushroom cultivation, or to any substance which is part of the mushroom growth substrate.

Preferred examples of mushrooms are edible mushrooms and mushrooms grown for pharmaceutical or industrial purposes. Examples of edible mushrooms are *Agaricus bisporus* (regular mushroom), *Pleurotus ostreatus* (oyster mushroom), *Lentinus edotus* (Shiitake mushroom), *Pholiota aegerita* (Poplar mushroom) and *Lepista nuda* (Blue stalk mushroom).

For the purpose of clarity and a concise description features are described herein as part of the same or separate embodiments, however, it will be appreciated that the scope of the invention may include embodiments having combinations of all or some of the features described

EXAMPLES

Example 1

Experiments were performed to search for an optimal surfactant combination which provides a stable, highly concentrated suspension of phosphite that is compatible to mixing with other agricultural active ingredients. All experiments were performed with 500 g/L Na2HPO3 and undissolved calcium lignosulfonate in the presence of a polyalkylene-oxide block copolymer (Synperonic PE/L61 (Croda); 0.9% (w/w)). A summary of the experiments is provided in Table 1.

CIPAC MT 46.3 (Accelerated storage procedures), by storing the formulations at 54° C. over a period of 2 weeks was applied to check whether a formulation is stable or not is.

From all tested combinations, a stable suspension was only obtained when using HELIWET NLS 90 (Mosselman s.a., B-7011 Ghlin, Belgium), in combination with Synperonic PE/L61.

The stabilizing effects of HELIWET NLS 90, in combination with Synperonic PE/L61, were found in the range of 0.5-5% (w/w) for HELIWET NLS 90, and 0.5-1.5% (w/w) for Synperonic PE/L61.

TABLE 1

| Surfactant combination used | | |
| --- | --- | --- |
| Anion surfactant | Non-ionic surfactant | Comment |
| Sodium di-octylsuccinate Emulsogen SF8 Liquid (Clariant) Dosage: 2.5-5% | | Phase separation within 24 hours |
| | Fatty alkoholethoxylate (30) Genapol EP 2584 (Clariant) Dosage: 2-4% | Highly insoluble and flocculation |

TABLE 1-continued

| Surfactant combination used | | |
|---|---|---|
| Anion surfactant | Non-ionic surfactant | Comment |
| Dodecylbenzenesulphonate Heloxyl AL 80 (Chempri) Dosage: 2.5-5% | | Phase separation within 7 days |
| | Polyoxyethylene C12-C15 alcohol (20) Synperonic A20 (Croda) Dosage: 2.5-5% | Phase separation within one hour |
| | Acrylic copolymer solution Atlox 4913 (Croda) Dosage: 3.5% | Flocculation formed immediately |
| | Polyarylphenol-ethoxylate phosphate Amm.salt Soprophor FL (Azelis) Dosage: 2-3% | Insoluble (direct phase separation) |
| Sulfonated Aromatic Polymer Morwet D425 (Akzo) Dosage: 2.5-5% | | Increase in viscosity at temperature >30 C. |
| | Polyoxyethylene-20 Sorbitan mono-laurate Tween 20 (Croda) Dosage: 3% | Flocculation formed immediately |
| Amine alkylbenzenesulfonate Zephrym 3300B (Croda) Dosage: 2-3% | | Increased viscosity at temperature >30 C. |
| Sodium-N-Methyl Oleyl Taurate Adinol OT-72 (Croda) Dosage: 2-4% | | Phase separation, increase viscosity. |
| Sodium dodecyl sulfate HELIWET NLS 90 (Mosselman s.a., B-7011 Ghlin, Belgium). Dosage: 1-5% | | Stable product |

Example 2

In this experiment, anionic surfactants were tested that have physical/chemical properties close to those of anionic surfactant Heliwet NLS 90.

These surfactants are:

1. Atlox 2575 (alkyl polysaccharide with CAS number 68515-73-1). Croda Crop Care, Snaith Goole, UK).
2. Metasperse 550S-PW-(WD) (styrene (meth)acrylic copolymer, Atlox Metasperse™ 550S (Croda Crop Care, Snaith Goole, UK).
3. Sodiumlaurylethersulfate (C12-C14 ethoxylated (2.5 e.o) sulfated sodiumsalt CAS:68891-38-3).
4. Sodiumlaurylsulphate Mackol CAS 100N (C12-C18 Sulfated sodiumsalt CAS:68955-19-1; Rhodia, France).

Testing of the different surfactants was performed in a phosphite-calcium lignosulfonate product. A stock solution (amounts of the compounds used: see Table 2 below) containing all ingredients except the anionic surfactant was prepared by subsequently:

Dissolving $H_3PO_3$ in water

Adding NaOH to a pH of 8.15

Adding calcium lignosulfonate

Adding Silcolapse 416 en Synperonic PE/L61

Mixing for at least 30 minutes

Addition of the anionic surfactant

Mixing for another 20 minutes

TABLE 2

Composition of the product in which the different anionic surfactants were tested.

| Compound | Amount (g/l) |
|---|---|
| $H_3PO_3$ (99% pure) | 325.4 |
| NaOH (99% pure) | 317.4 |
| $H_2O$ | 586.3 |
| Calciumlignosulfonate | 125.0 |
| Anionic surfactant* | 20.9 |
| Synperonic PE/L61 | 12.5 |
| Silcolapse 416 | 2.5 |

After mixing of the anionic surfactant in the product, the resulting mixture was milled on a bead mill apparatus for 25 minutes.

Test results:

After milling the products with the different anionic surfactants were stored at 4 and 40° C.

Results of the CIPAC tests MT46.1 (accelerated storage at high temp) and MT 39.1 (low temperature storage stability) are shown in Table 3.

TABLE 3

Anionic surfactants used

| Anionic surfactant used in the product | Observation during storage at 4° C. | Observation during storage at 40° C. | Product stability |
|---|---|---|---|
| Atlox 2575 | At 4° C., the product became very viscous (almost solid) within 1 week | Solution contained large lumps within 1 week | Not stable |
| Metasperse 550S | At 4° C. the product became very viscous (almost solid) within 1 week | Phase separation in three layers within 1 week | Not stable |
| Sodiumlaurylethersulfate | At 4° C. the product became very viscous (almost solid) within 1 week | Phase separation: large top layer with very high viscosity (almost solid) and bottom layer low viscosity, within 1 week | Not stable |
| Sodiumlaurylsulphate Mackol CAS 100N | Good viscosity no phase separation within 2 weeks | Increase in viscosity, no phase separation within 2 weeks | Not stable |
| Heliwet NLS 90 (sodiumlaurylsulphate type) | Good viscosity no phase separation within 2 weeks | Good viscosity no phase separation within 2 weeks | Stable product |

The results show that the formulation containing Heliwet NLS 90 was stable after 14 days of storage at 4 and 40° C. The product with sodiumlaurylsulphate Mackol CAS 100N remained stable at 4° C. but the viscosity of the product increased at 40° C. making the product not stable according to Cipac standards. These surfactants are very similar: both are non-ethoxylated sulfated sodium salts. The only difference is that Heliwet NLS 90 has a molecular chain length of C12-C14 and sodiumlaurylsulphate Mackol CAS 100N has a chain length of C12-C18. The other surfactants that are physical/chemical related to Heliwet NLS90 resulted to in clearly unstable products.

The invention claimed is:

1. A stable aqueous suspension of phosphite comprising a solubilized phosphite salt at 20-50% (w/w), insolubilized lignosulfonate at 2-30% (w/w), a dodecyl sulfate salt as an insolubilized anionic surfactant at 0.5-10% (w/w), and an ethylene oxide/propylene oxide block copolymer at 0.2-3% (w/w).

2. The suspension according to claim 1, wherein the solubilized phosphite salt is disodium hydrogen phosphite.

3. The suspension according to claim 1, wherein the anionic surfactant is sodium dodecyl sulfate.

4. The suspension according to claim 1, wherein the ethylene oxide/propylene oxide block copolymer is polyoxypropylene that is flanked by two chains of polyoxyethylene.

5. The suspension according to claim 4, wherein the block polymer has a molecular mass of about 2000 g/mol and a 10% polyoxyethylene content by weight.

6. The suspension according to claim 1, wherein the average particle size is between 0.2 and 5 micrometers.

7. A method of fertilizing an agricultural plant, comprising applying to said agricultural plant the suspension according to claim 1.

8. A method of protecting an agricultural plant or plant part against a pathogen, comprising applying to said agricultural plant or to said plant part the suspension according to claim 1.

9. A method of preventing, reducing and/or eliminating the presence of a pathogen on a plant or on one or more plant parts, comprising applying to said plant or plant part the suspension according to claim 1.

10. The method of claim 8, wherein the plant part comprises seed, leaf or fruit.

11. A method for treatment of a soil, comprising
a) providing the suspension according to claim 1; and
b) adding the suspension to the soil.

12. The method according to claim 8, wherein the suspension is diluted with an aqueous liquid and mixed with a fungicide prior to application to said plant or plant part.

13. The method according to claim 10, wherein the plant part is a post-harvest fruit.

14. The method according to claim 9, wherein the plant part comprises seed, leaf or fruit.

15. The method according to claim 14, wherein the plant part is a post-harvest fruit.

16. The method according to claim 11, wherein the soil is a growth substrate for mushrooms.

17. The method according to claim 12, wherein the fungicide is a metal-containing fungicide.

18. The method according to claim 11, wherein the suspension is diluted with an aqueous liquid and mixed with a fungicide prior to application to said soil.

19. A method of producing a stable aqueous suspension of phosphite, said method comprising
providing a 10-50% (w/w) aqueous solution of a solubilized phosphite salt,
adding 2-20% (w/w) of powderous lignosulfonate to said solution,
adding 0.5-10% (w/w) of powderous dodecyl sulfate salt, and
adding 0.2-2% (w/w) of an ethylene oxide/propylene oxide block copolymer.

20. The method of producing an aqueous suspension according to claim 19, further comprising crushing the resulting suspension to an average particle size of between 0.2 and 5 micrometers.

21. The method according to claim 20, whereby the suspension is crushed by milling.

* * * * *